United States Patent [19]

Diblitz et al.

[11] Patent Number: 5,241,068
[45] Date of Patent: Aug. 31, 1993

[54] HETEROCYCLIC COMPOUNDS

[75] Inventors: Christina Diblitz, Kaarst; Hans Höchstetter, Bad Berneck, both of Fed. Rep. of Germany

[73] Assignee: Bayer Aktiengesellschaft, Leverkusen, Fed. Rep. of Germany

[21] Appl. No.: 748,310

[22] Filed: Aug. 21, 1991

[30] Foreign Application Priority Data

Aug. 31, 1990 [DE] Fed. Rep. of Germany ....... 4027607

[51] Int. Cl.⁵ ................. C07D 211/02; C07D 213/08; C07D 213/14
[52] U.S. Cl. .................. 544/250; 544/249; 544/385; 8/509
[58] Field of Search ......... 544/349, 350, 385

[56] References Cited

U.S. PATENT DOCUMENTS

| | | | |
|---|---|---|---|
| 4,206,114 | 10/1981 | Appleton et al. | 544/350 |
| 4,289,759 | 9/1981 | Heavner et al. | 544/385 |
| 4,417,014 | 11/1983 | Buecheler | 544/245 |

FOREIGN PATENT DOCUMENTS

| | | |
|---|---|---|
| 1196205 | 7/1965 | Fed. Rep. of Germany. |
| 3830096 | 3/1990 | Fed. Rep. of Germany. |
| 2301570 | 9/1976 | France. |
| 3112568 | 5/1988 | Japan ................... 544/385 |
| 3290868 | 11/1988 | Japan ................... 544/385 |
| 1-013074 | 1/1989 | Japan ................... 544/385 |
| 1-013075 | 1/1989 | Japan ................... 544/385 |

*Primary Examiner*—Cecilia Tsang
*Attorney, Agent, or Firm*—Sprung Horn Kramer & Woods

[57] ABSTRACT

Compounds of the formulae

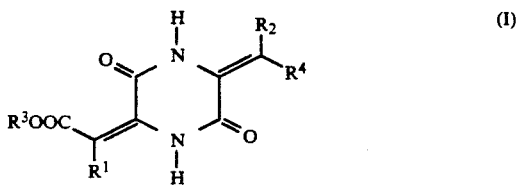
(I)

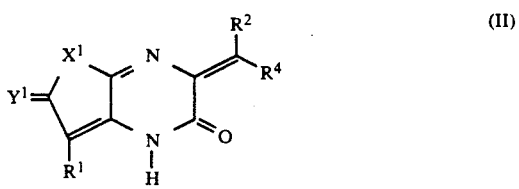

(II)

in which $R^1$, $R^2$, $R^3$, $R^4$, $X^1$ and $Y^1$ have the stated meanings, processes for their preparation and their use.

4 Claims, No Drawings

HETEROCYCLIC COMPOUNDS

The invention relates to heterocyclic compounds which, in one of their tautomeric or configurational isomer forms, correspond to the formulae

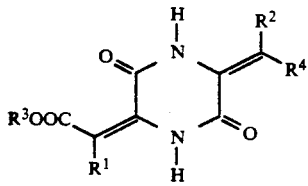

and

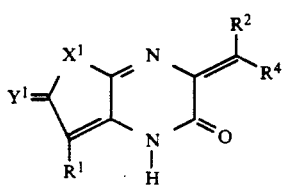

compounds of the formula

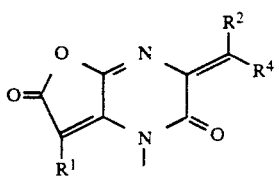

also being of particular interest.

The substituents in the formulae I–III have the following meanings:

$R^1$ and $R^2$ = optionally substituted alkyl, optionally substituted cycloalkyl, optionally substituted aralkyl, optionally substituted aryl or an optionally substituted heterocyclic radical which has a double bond having at least one C atom, in particular >C=C< and >C=N— in conjugation with the exocyclic double bond of I or with the C=C— bond in the five-membered rings in II or III, $R^3$, $R^4$ and $R^5$ = hydrogen, optionally substituted alkyl, optionally substituted aryl, optionally substituted cycloalkyl, optionally substituted aralkyl or an optionally substituted heterocyclic radical and $X^1$ and $Y^1$ = O, S, $NR^5$, in particular —N-aryl; $X^1$ and $Y^1$ may furthermore each form parts of a fused-on heterocyclic five-membered or six-membered ring which then preferably contains 2N atoms.

The invention furthermore relates to processes for the preparation of the compounds I to III and their use.

Alkyl preferably represents $C_1$–$C_{18}$-alkyl, in particular $C_1$–$C_4$-alkyl. Cycloalkyl preferably presents $C_3$–$C_7$-cycloalkyl, in particular cyclohexyl and cyclopentyl. Examples of suitable substituents of the alkyl and cycloalkyl radicals are: halogen, such as Cl, Br, F, CN, $OCOR^{10}$, $OR^7$, $COOR^{10}$, $SR^7$, $CONR^8R^9$ and $OCONR^8R^9$, in which $R^7$ to $R^{10}$ have the meanings stated below.

Aralkyl represents, in particular, phenyl- and naphthyl$C_1$–$C_4$-alkyl, in which the aryl radicals may be substituted, for example as stated below for aryl.

Aryl preferably represents carbocyclic-aromatic radicals which contain 1, 2, 3 or 4, in particular 1 or 2, rings such as phenyl, biphenylyl and naphthyl.

Preferred heterocyclic radicals are heterocyclic (aromatic) radicals which contain 1, 2, 3 or 4, in particular 1 or 2, five-membered, six-membered or seven-membered rings, at least one of which contains 1, 2 or 3, preferably 1 or 2, hetero atoms from the series consisting of O, N and S. The following may be mentioned as examples of heterocyclic radicals: pyridyl, pyrimidyl, pyrazinyl, triazinyl, furoyl, pyrrolyl, thiophenyl, quinolyl, cumarinyl, benzofuranyl, benzimidazolyl, benzoxazolyl, dibenzofuranyl, benzothiophenyl, dibenzothiophenyl, indolyl, carbazolyl, pyrazolyl, imidazolyl, oxazolyl, isoxazolyl, thiazolyl, indazolyl, benzothiazolyl, pyridazinyl, cinnolyl, quinazolyl, quinoxalyl, phthalazinyl, phthalazindionyl, phthalamidyl, chromonyl, naphtholactamyl, quinolonyl, ortho-sulphobenzimidyl, maleimidyl, naphtharidinyl, benzimidazolonyl, benzoxazolonyl, benzothiazolonyl, benzothiazothionyl, quinazolonyl, quinoxalonyl, phthalazonyl, dioxopyrimidinyl, pyridonyl, isoquinolonyl, isoquinolinyl, isothiazolyl, benzoisoxazolyl, benzoisothiazolyl, indazolonyl, acridinyl, acridonyl, quinazolinedionyl, quinoxalinedionyl, benzoxazinedionyl, benzoxazinonyl and naphthalimidyl.

The aryl and heterocyclic radicals may be substituted, for example, by halogen, such as chlorine, bromine and fluorine, —CN, $R^6$, $OR^7$, $SR^7$, $NR^8R^9$, $COOR^{10}$, $COR^{10}$, $NR^8COR^{10}$, $NR^8COOR^{10}$, $NR^8CONR^8R^9$, $NHSO_2R^{10}$, $SO_2R^{10}$, $SO_2OR^{10}$, $CONR^8R^9$, $SO_2NR^8R^9$, N=N—$R^{11}$, $OCOR^{10}$ and $OCONR^8R^9$.

$R^6$ designates optionally substituted alkyl, preferably $C_1$–$C_{18}$-alkyl, in particular $C_1$–$C_4$-alkyl, and optionally substituted cycloalkyl, preferably $C_3$–$C_7$-cycloalkyl, in particular cyclohexyl and cyclopentyl.

Examples of suitable substituents of the alkyl and cycloalkyl radicals $R^6$ are: halogen, such as Cl, Br, F, CN, $OCOR^{10}$, $OR^7$, $COOR^{10}$, $SR^7$, $CONR^8R^9$ and $OCONR^8R^9$.

$R^7$, $R^8$, and $R^9$ designate hydrogen, optionally substituted alkyl, in particular $C_1$–$C_{18}$-alkyl, preferably $C_1$–$C_4$-alkyl, optionally substituted cycloalkyl, in particular cyclohexyl and cyclopentyl, optionally substituted aralkyl, in particular phenyl- and naphthyl-$C_1$–$C_4$-alkyl, optionally substituted aryl, in particular phenyl and naphthyl, and an optionally substituted heterocyclic radical, in particular the radical of a 5-membered or 6-membered heterocyclic ring having 1, 2 or 3 hetero atoms from the series consisting of O, N and S, to which a benzene ring may be fused.

The alkyl and cycloalkyl radicals $R^7R^8$ and $R^9$ may be substituted, for example, by Cl, Br, F, CN, mono-$C_1$–$C_4$-alkylamino, di-$C_1$–$C_4$-alkylamino, phenyl or naphthyl, which may be substituted by Cl, Br, F, $C_1$–$C_6$-alkyl and $C_1$–$C_6$-alkoxy or by heterocyclic radicals of a 5-membered or 6-membered heterocyclic ring system having 1 or 2 hetero atoms from the series consisting of O, N and S, to which a benzene ring may be fused.

Furthermore, $R^8$ and $R^9$ together, including the N atom, may form a 5-membered or 6-membered heterocyclic ring, for example a morpholine, piperidine or phthalimide ring. The aryl and aralkyl radicals $R^8$ and $R^9$ may be substituted, for example, by Cl, Br, F, $C_1$–$C_{18}$-alkyl, preferably $C_1$–$C_4$-alkyl, or $C_1$–$C_{18}$-alkoxy, preferably $C_1$–$C_4$-alkoxy.

$R^{10}$ designates hydrogen, optionally substituted alkyl, in particular $C_1-C_{18}$-alkyl, preferably $C_1-C_4$-alkyl, optionally substituted cycloalkyl, in particular cyclopentyl and cyclohexyl, optionally substituted aralkyl, in particular phenyl- and naphthyl-$C_1-C_4$-alkyl, preferably benzyl, or optionally substituted aryl, in particular phenyl and naphthyl.

The radicals stated for $R^{10}$ may be substituted in the same way as the corresponding radicals $R^8$ and $R^9$.

$R^{11}$ designates the radical of a coupling component, preferably of a coupling component from the benzene, naphthalene, acetoacetarylide, pyrazole or pyridone series, or a phenyl radical which is optionally substituted by Cl, Br, F, $C_1-C_{18}$-alkyl, preferably $C_1-C_4$-alkyl and $C_1-C_{18}$-alkoxy, preferably $C_1-C_4$-alkoxy.

For the preparation of compounds of the formula I, compounds of the formula

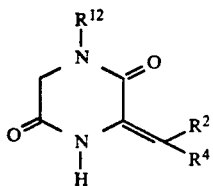

IV which are known from the literature or can be prepared analogously to processes known from the literature are reacted with compounds of the formula $$R^1-COCOOR^3 \quad V.$$

The radical $R^{12}$ may denote hydrogen or $COR^5$, $R^1$ to $R^5$ having the meanings stated above.

The reaction is preferably carried out in the presence of a basic catalyst. Aliphatic amines, in particular tertiary aliphatic amines, such as triethylamine, are suitable. The amines are preferably used in equimolar amounts.

The reaction is preferably carried out at a temperature of from 30° to 130° C., particularly preferably from 50° to 100° C.

The reaction can be carried out without solvents. However, it can also be carried out in solvents. For example, alcohols or dipolar aprotic solvents, such as acetonitrile, dimethyl sulphoxide and in particular dimethylformamide are suitable.

In the reaction according to the invention, all four possible configurational isomers I a, I b, I c and I d are generally formed.

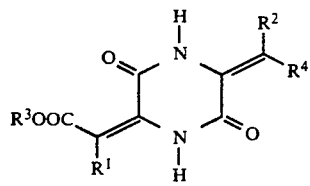

Ia

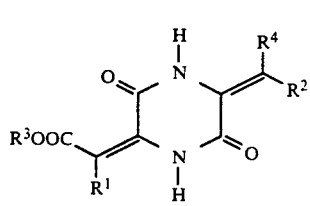

Ib

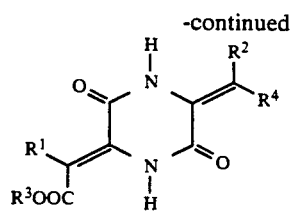

Ic

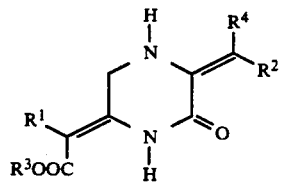

Id

Compounds of the formula III can be prepared, for example, by heating piperazine derivatives of the formula I in the melt or in high-boiling solvents. Compounds of the formula III are also formed when compounds I are heated in the presence of a suitable catalyst or in dehydrating agents, such as acetic anhydride or phosphorus oxychloride. Examples of suitable solvents are o-dichlorobenzene or high-boiling aromatic hydrocarbons or ethers, and an example of a suitable catalyst is p-toluenesulphonic acid or sulphuric acid. The reaction is preferably carried out at temperatures between 100° and 240° C., particularly preferably 120°–160° C.

Compounds of the formula II in which $X^1=NR^5$ are prepared by reacting compounds of the formula I or III with virtually any primary amines in high-boiling solvents, optionally in the presence of a suitable catalyst, with elimination of water or of water and alcohol. Compounds of the formula III have similar reactivity to aromatic carboxylic anhydrides, for example perylenetetracarboxylic dianhydride.

As already mentioned, virtually any primary amine may be used, and even sterically severely hindered amines, such as 2,6-diethyl-4-methylaniline, or very weakly basic amines, such as aromatic amines containing nitro groups or cyano groups, react to give the compounds of the formula III. Low-boiling aliphatic amines can, if required, be reacted in an autoclave.

Compounds of the formula VII as described below and in which $R^5=$hydrogen are prepared by heating compounds of the formula I in formamide.

Examples of suitable high-boiling solvents for carrying out the reaction according to the invention are: (chlorinated) aromatic hydrocarbons such as xylene, chlorobenzene, dichlorobenzenes, trichlorobenzenes, naphthalene or chloronaphthalene. Quinoline is particularly suitable. However, water can also be used (in an autoclave) or the relavent amine itself can act as a solvent if it has a sufficiently high boiling point. It may prove advantageous to remove the resulting water of reaction azeotropically.

The reaction preferably takes place at temperatures of 130° to 250° C., particularly preferably between 180° and 210° C.

Suitable catalysts are mineral acids, carboxylic acids, sulphonic acids or metal salts, for example zinc acetate or zinc chloride.

Compounds of the formula II in which $X^1=S$ are prepared by exchanging the O atoms in III for S, for example by sulphurisation with Lawesson's reagent or with anhydrous $H_2S$.

For the preparation of compounds of the formula II in which $X^1$ and $Y^1$ form parts of a fused-on heterocyclic five-membered or six-membered ring having 2 N atoms, compounds II are reacted with primary aromatic diamines, for example 1,8-diaminonaphthalene or o-phenylenediamines. A typical compound of this type is illustrated by the following formula:

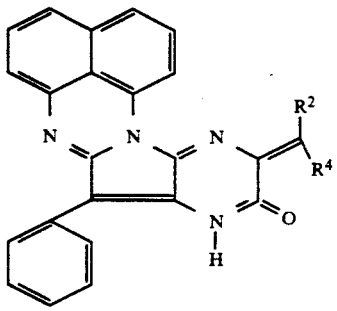

Preferred compounds of the formula II are those which correspond to the formula

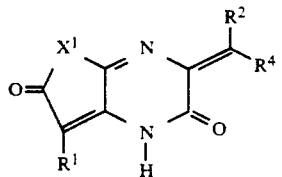

VI and in particular to the formula

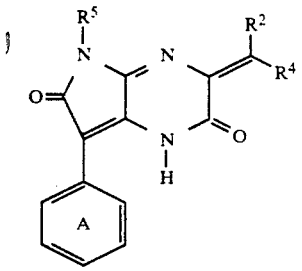

VII in which $R^2$, $R^4$, $R^5$ and $X^1$ have the meanings stated above and the ring designated by A may be substituted, for example by halogen, such as Cl, Br or F, —NHCOR$^8$ and/or —NR$^8$R$^9$, in which $R^8$ and $R^9$ have the meanings stated above.

The compounds of the formula I are used in particular as intermediates for the preparation of valuable dyes and pigments, in particular for the preparation of compounds III.

Compounds of the formula III can be used as dyes or as intermediates for the preparation of dyes or pigments, in particular II. Thus, the compounds of the formula III can be used as soluble dyes for colouring plastics (polystyrene) or else as disperse dyes, optionally after prior introduction of lipophilic radicals.

Compounds of the formula II can be used in particular as colorants, for example for pigmenting or dyeing high molecular weight organic material, particularly preferably plastics.

Homopolymers and copolymers based on polycarbonate, polystyrene, polyacrylate, polymethacrylate, polymethyl acrylate and polymethyl methacrylate may be mentioned as examples of plastics.

The preparation and working up of the compounds of the formulae II and III can be controlled in such a way that they are obtained in a form suitable for use as dyes, in particular as plastics-soluble dyes, or as pigments.

The following may be mentioned as examples of suitable thermoplastics which can be dyed or pigmented with the colorants according to the invention: cellulose esters, such as cellulose nitrate, cellulose acetate, cellulose triacetate, cellulose acetobutyrate or cellulose propionate, cellulose ethers, such as methylcellulose, ethylcellulose or benzylcellulose, linear saturated polyester resin plastics, aniline resin plastics, polycarbonates, polystyrene, polyvinylcarbazole, polyvinyl chloride, in particular rigid PVC, polymethacrylates, polyvinylidene chloride, polyacrylonitrile, polyoxomethylenes, linear polyurethanes and copolymers, such as vinyl chloride/vinyl acetate copolymers and in particular styrene copolymers, such as styrene/acrylonitrile copolymers (SAN), styrene/butadiene copolymers (SB) and styrene/α-methylstyrene copolymers (SMS).

The high molecular weight compounds mentioned may be present individually or as mixtures, plastic masses or melts, which, if required, can be spun into fibres.

The novel process is particularly suitable for the mass colouring of polystyrene, in particular for the mass colouring of poly(meth)acrylates, preferably polymethyl methacrylate.

The plastics to be coloured, advantageously in the form of powders, chips or granules, are thoroughly mixed with the dye. This may be effected, for example, by coating the plastics particles with the finely divided dry dye powder or by treatment of the particles with a solution or dispersion of the dye in an organic solvent and subsequent removal of the solvent.

In the process according to the invention, it is also possible to use mixtures of different dyes of the formula II and/or mixtures of dyes of the formula II with other dyes and/or inorganic or organic pigments.

The process according to the invention can also be carried out by a procedure in which the dye is added to the monomer (mixture) or to a prepolymer before or during the polymerisation, for example by dissolving the dye in the monomer (mixture).

The ratio of dye to plastic may vary within wide limits, depending on the desired colour strength. In general, it is advisable to use 0.005–30 parts, preferably 0.01–3 parts, of dye per 100 parts of plastic.

The treated polymer particles are melted by known methods in an extruder and are extruded to give articles, for example films or fibres, or cast into sheets.

Colouring of the plastics with the dyes of the formula II is carried out, for example, by a procedure in which such a dye, optionally in the form of masterbatches, is mixed with these substrates using roll mills, mixing apparatuses or milling apparatuses. The coloured material is then brought into the desired final form by methods known per se, such as calendering, pressing, extrusion, spreading, casting or injection moulding.

For the production of non-rigid mouldings or for reducing their brittleness, it is often desirable to incorporate plasticisers in the high molecular weight compounds prior to moulding. For example, esters of phosphoric acid, phthalic acid or sebacic acid can be used as such. In the process according to the invention, the plasticisers can be incorporated into the polymers before or after incorporation of the dye.

The compounds of the formula II are obtained in a form suitable for use of the pigment or can be converted into the suitable form by aftertreatment processes known per se, for example by dissolution or swelling in strong inorganic acids, such as sulphuric acid, and discharge onto ice. Fine division can also be achieved by milling with or without grinding media, such as inorganic salts or sand, optionally in the presence of solvents such as toluene, xylene, dichlorobenzene or N-methylpyrrolidone.

The colour strength and transparency of the pigment can be influenced by varying the aftertreatment.

Because of their lightfastness and fastness to migration, the compounds of the formula II are suitable for a very wide range of pigment applications. Thus, they can be used for the production of very fast pigmented systems when mixed with other substances, formulations, coating agents, printing inks, coloured paper and coloured macromolecular substances. Mixtures with other substances may be understood, for example, as meaning those with inorganic white pigments, such as titanium dioxide (rutile) or with cement. Formulations are, for example, flush pastes containing organic liquids or pastes and fine pastes with water, dispersants and optionally preservatives. The term coating agent represents, for example, physically or oxidatively drying coatings, stoving enamels, reactive coatings, two-component coatings, emulsion paints for weather-resistant coatings and distempers.

Printing inks are understood as meaning those for paper, textile and tinplate printing. The macromolecular substances may be of natural origin, such as rubber, obtained by chemical modification such as acetylcellulose, cellulose butyrate or viscose, or synthetically produced, such as polymers, polyadducts and polycondensates. Plastic materials, such as polyvinyl chloride, polyvinyl acetate, polyvinyl propionate, polyolefins, for example polyethylene, or polyamides, superpolyamides, polymers and copolymers of acrylates, methacrylates, acrylonitrile, acrylamide, butadiene or styrene and polyurethanes and polycarbonates may be mentioned. The substances pigmented with the claimed products may also be in any form.

The pigments of the formula II furthermore have excellent fastness to water, fastness to oil, fastness to acid, fastness to lime, fastness to alkalis, fastness to solvents, fastness to overcoating, fastness to overspraying, fastness to sublimation, heat resistance and resistance to vulcanisation and have very high colouring power and can be readily distributed in plastic materials.

EXAMPLE 1

8.2 g of 3-m-chlorobenzylidene-piperazine-2,5-dione, 4.8 g of methyl phenylglyoxylate and 3.0 g of triethylamine are stirred for 5 hours at 60° C. Thereafter, the triethylamine is substantially stripped off in vacuo and the oily crystalline residue is stirred with 15 ml of methanol for 12 hours. The mixture is then cooled to 0° C. and stirred for a further 2 hours and the product is filtered off under suction and washed with ice-cold methanol. 8.2 g of the isomer mixture of

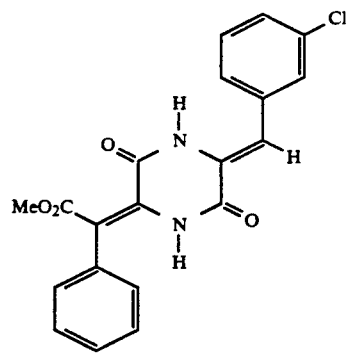

are obtained as a yellowish white crystalline substance.

EXAMPLE 2

5 g of the isomer mixture obtained in Example 1, in 20 ml of DMF, are heated for 8 hours at 100° C. After cooling, the product is filtered off under suction and washed with methanol. 3.8 g of a greenish yellow powder are obtained.

UV (DMF):$\lambda_{max}$=384 nm (27,000)

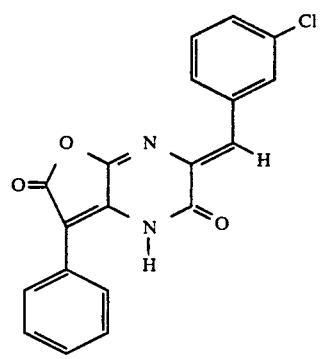

ps Incorporation of this substance in polystyrene gives a greenish yellow colour.

EXAMPLE 3

7 g of 3-p-methoxy-benzylidenepiperazine-2,5-dione, 2 g of methyl phenylglyoxylate and 3.6 g of triethylamine, in 50 ml of DMF, are stirred for 8 hours at 100° C. The precipitate formed is filtered off under suction at room temperature and 30 ml of methanol are added to the mother liquor. Further product is precipitated as orange-yellow crystalline powder. A total of 6.2 g of product are obtained.

UV (DMF):$\lambda_{max}$=409 nm (25,300)

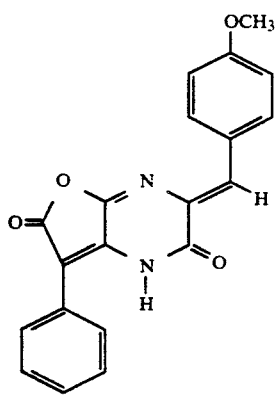

EXAMPLE 4

7 g of the isomer mixture prepared according to Example 3 are stirred together with 1.3 g of p-methoxyaniline and 0.1 g of zinc acetate in 20 ml of quinoline for 2 hours at 190°–200° C. The mixture is cooled to 65° C. and then stirred with 30 ml of ethanol, and the product is filtered off under suction. 2.8 g of a yellow-orange, crystalline dye of the formula

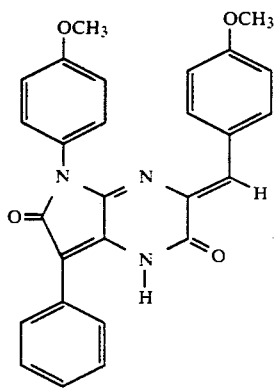

UV (DMF): $\gamma_{max}$ = 420 (36,600)

are isolated, the said dye giving a yellow colour when incorporated in polystyrene.

EXAMPLE 5

4.0 g of the isomer mixture obtained in Example 2 are boiled under reflux together with 2 g of p-methoxyaniline and 50 mg of p-toluenesulphonic acid in 30 ml of o-dichlorobenzene for 12 hours. After filtration under suction at room temperature, 2.3 g of the compound

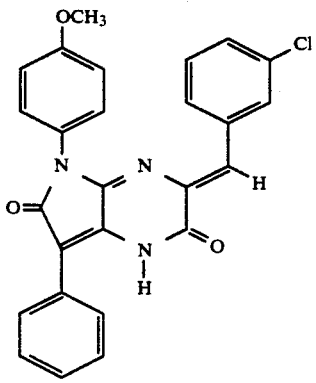

UV (DMF): $\gamma_{max}$ = 399 nm (30,000)

are isolated, the said compound giving a yellow colour in polystyrene.

The following compounds of table 1 were prepared according to Examples 4 and 5.

TABLE 1

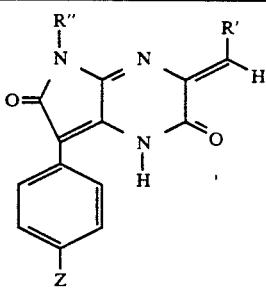

| Example no. | Z | R' | R" | Remarks |
|---|---|---|---|---|
| 6 | H | —⟨C6H4⟩—OCH3 | n-Butyl | yellow dye |

TABLE 1-continued

[Structure: pyrazine-based compound with R''-N, N, R'-CH substituents, two C=O groups, NH, and phenyl ring with Z substituent]

| Example no. | Z  | R'              | R''              | Remarks    |
|-------------|----|-----------------|------------------|------------|
| 7           | Cl | 4-OCH₃-phenyl   | n-Butyl          | yellow dye |
| 8           | H  | 4-OCH₃-phenyl   | CH₃              | yellow dye |
| 9           | Cl | 4-OCH₃-phenyl   | CH₃              | yellow dye |
| 10          | H  | 4-OCH₃-phenyl   | Hexadecyl        | yellow dye |
| 11          | H  | 4-OCH₃-phenyl   | —CH₂—CH₂—OH      | yellow dye |
| 12          | H  | 4-OCH₃-phenyl   | phenyl           | yellow dye |
| 13          | Cl | 4-OCH₃-phenyl   | phenyl           | yellow dye |
| 14          | H  | 4-OCH₃-phenyl   | 4-Cl-phenyl      | yellow dye |
| 15          | H  | 4-Cl-phenyl     | 4-OCH₃-phenyl    | yellow dye |
| 16          | H  | 4-Cl-phenyl     | 4-Cl-phenyl      | yellow dye |
| 17          | H  | 4-Cl-phenyl     | 3-Cl-phenyl      | yellow dye |

TABLE 1-continued
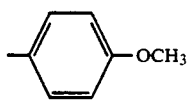
| Example no. | Z | R' | R" | Remarks |
|---|---|---|---|---|
| 18 | H | 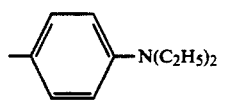 —OCH$_3$ | 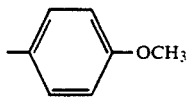 —N(C$_2$H$_5$)$_2$ | greenish yellow dye |
| 19 | Cl | 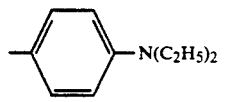 —OCH$_3$ | 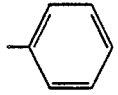 —N(C$_2$H$_5$)$_2$ | greenish yellow dye |
| 20 | H | 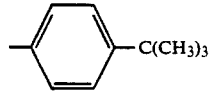 | 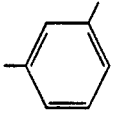 —C(CH$_3$)$_3$ | yellow dye |
| 21 | H | 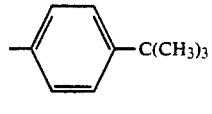 Cl | 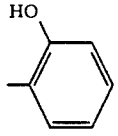 —C(CH$_3$)$_3$ | yellow dye |
| 22 | H | 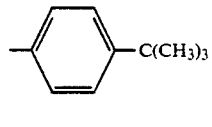 HO | 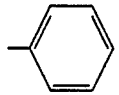 —C(CH$_3$)$_3$ | yellow dye |
| 23 | H | 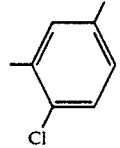 | 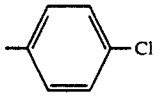 Cl, Cl | yellow dye |
| 24 | Cl | 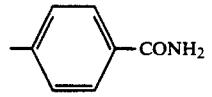 —Cl | 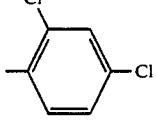 —CONH$_2$ | yellow dye |
| 25 | H | 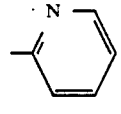 Cl, Cl | 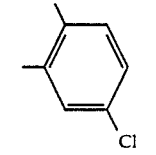 N (pyridyl) | yellow dye |
| 26 | Cl | 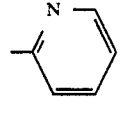 Cl, Cl | N (pyridyl) | yellow dye |

TABLE 1-continued

| Example no. | Z | R' | R" | Remarks |
|---|---|---|---|---|
| 27 | H | 2,4-dichlorophenyl | 4-(2-acetylamino-anilino)phenyl | yellow dye |
| 28 | Cl | 2,4-dichlorophenyl | 4-(2-acetylamino-anilino)phenyl | yellow dye |
| 29 | H | 4-methoxyphenyl | 2-benzimidazolyl | yellow dye |
| 30 | Cl | 4-chlorophenyl | 2-benzimidazolyl | yellow dye |
| 31 | H | 2,5-diethyl-4-methylphenyl | 2-cyanophenyl | yellow dye |
| 32 | Cl | 3-acetylaminophenyl | 2-cyano-4-chlorophenyl | yellow dye |
| 33 | H | 3-acetylaminophenyl | 2,5-dimethylphenyl | yellow dye |

TABLE 1-continued
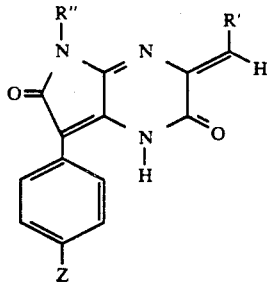
| Example no. | Z | R' | R'' | Remarks |
|---|---|---|---|---|
| 34 | Cl | 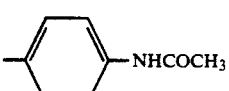 —NHCOCH₃ | 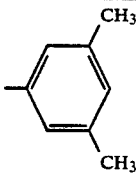 2,5-(CH₃)₂ | yellow dye |
| 35 | H | 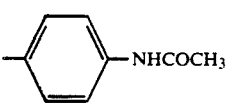 —NHCOCH₃ | 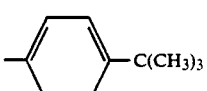 —C(CH₃)₃ | yellow dye |
| 36 | Cl | 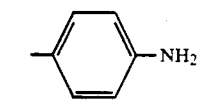 —NH₂ | 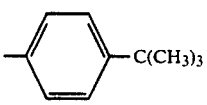 —C(CH₃)₃ | yellow dye |
| 37 | H | 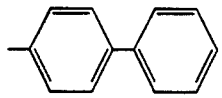 biphenyl | 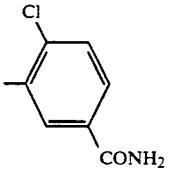 4-Cl, 3-CONH₂ | yellow dye |
| 38 | Cl | 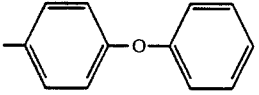 —O-phenyl | 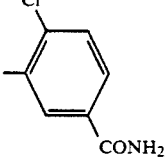 4-Cl, 3-CONH₂ | yellow dye |
| 39 | H | 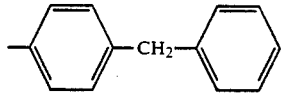 —CH₂-phenyl | 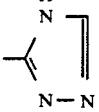 triazole | yellow dye |
| 40 | Cl | 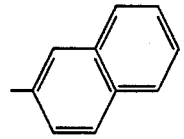 naphthyl | 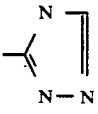 triazole | yellow dye |
| 41 | H | 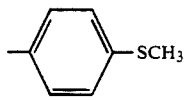 —SCH₃ | 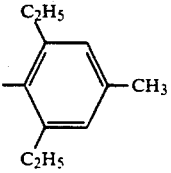 2,5-(C₂H₅)₂, 4-CH₃ | yellow dye |

EXAMPLE 42 (Use Example)

0.1 g of the dye of the formula

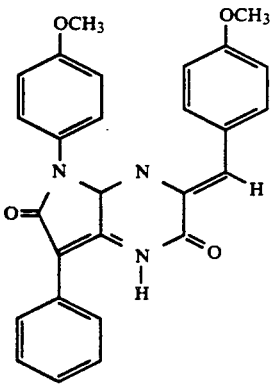

2 g of titanium dioxide (Bayertitan ® R-FK-2) and 100 g of polystyrene granules are mixed in a closed vessel for 2 hours on a roller stand. The mixture obtained is extruded at about 230° C. to give 2 cm wide extrudates, which are granulated again. The granules are injection moulded with the aid of an injection moulding machine at 230°-240° C. to give mouldings. Yellow mouldings having high heat resistance and good lightfastness are obtained.

EXAMPLE 43

0.02 g of the dye of the formula stated in Example 42 and 100 g of polystyrene granules are mixed in a closed vessel for 2 hours on a roller stand. The mixture is then injection moulded at 230°-240° C. with the aid of a screw-type injection moulding machine to give mouldings. The yellow, transparent mouldings have good lightfastness and high heat resistance.

EXAMPLE 44

100 g of a commercial polycarbonate in the form of granules are dry blended with 0.01 g of the dye of the formula stated in Example 42. The granules thus obtained are homogenised in a twin-screw extruder at 290° C. A transparent yellow colour of good lightfastness is obtained. The coloured polycarbonate is extruded from the extruder in strand form and converted into granules. The granules can be processed by the customary methods for compounding thermoplastic materials.

EXAMPLE 45

0.03 g of the dye of the formula stated in Example 42 is dissolved in 99.97 g of methyl methacrylate. After the addition of 0.1 g of dibenzoyl peroxide, the solution is heated to 120° C. and the polymerisation initiated. After 30 minutes, the partially polymerised methyl methacrylate is completely polymerised between two glass plates at 80° C. in the course of ten hours. Yellow, transparent polymethacrylate sheets are obtained.

We claim:

1. Compounds which, in one of their tautomeric or configurational isomer forms, correspond to the formula

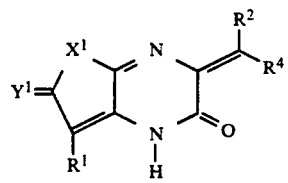

$R^1$ and $R^2$ represent:
$C_1$–$C_{18}$ alkyl or $C_3$–$C_7$ cycloalkyl optionally substituted by halogen, CN, $OCOR^{10}$, $OR^7$, $COOR^{10}$, $SR^7$, $CONR^8R^9$, or $OCONR^8R^9$, in which $R^7$ to $R^{10}$ have the meanings stated hereafter,
aryl or aralkyl group selected from the group consisting of phenyl, biphenyl, naphthyl, phenyl-$C_1$–$C_4$ alkyl, naphthyl-$C_1$–$C_4$ alkyl, wherein the aryl or aralkyl radical are optionally substituted by halogen, —CN, $R^6$, $OR^7SR^7$, $NR^8R^9$, $COOR^{10}$, $COR^{10}$, $NR^8COR^{10}$, $NR^8COOR^{10}$, $NR^8CONR^8R^9$, $NHSO_2R^{10}$, $SO_2R^{10}$, $SO_2OR^{10}$, $CONR^8R^9$, $SO_2NR^8R^9$, $N=N-R^{11}$, $OCOR^{10}$ or $OCONR^8R^9$, in which $R^7$ to $R^{10}$ have the meanings stated hereafter.
$R^4$ represents hydrogen or one of the groups listed above for $R^1$ or $R^2$,
$X^1$ and $Y^1$ represent O, S, $NR^5$,
$R^5$ represents hydrogen or one of the groups listed above for $R^1$ or $R^2$, or one of the following groups:

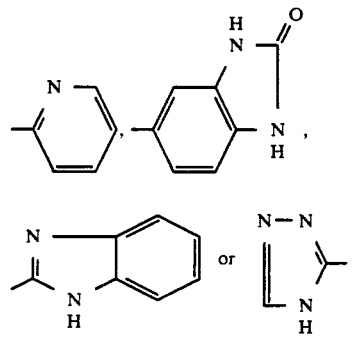

$R^6$ represents $C_1$–$C_{18}$ alkyl or $C_3$–$C_7$ cycloalkyl optionally substituted by halogen, CN, $OCOR^{10}$, $OR^7$, $COOR^{10}$, $SR^7$, $CONR^8R^9$ or $OCONR^8R^9$,
$R^7$, $R^8$, and $R^9$ represent hydrogen, $C_1$–$C_{18}$ alkyl, $C_3$–$C_7$ cycloalkyl, alkyl or aralkly group selected from the group consisting of phenyl-$C_1$–$C_4$ alkyl, naphthyl-$C_1$–$C_4$, phenyl and naphthyl, wherein the alkyl and cycloakyl groups are optionally substituted by Cl, Br, F, CN, mono-$C_1$–$C_4$-alkylamino, di-$C_1$–$C_4$-alkylamino, phenyl or naphthyl which are optionally substituted by Cl, Br, F, $C_1$–$C_6$-alkyl or $C_1$–$C_6$-alkoxy and wherein the aryl and aralkyl groups are optionally substituted by Cl, Br, F, $C_1$–$C_6$-alkyl or $C_1$–$C_6$-alkoxy, or
$R^{10}$ represents hydrogen, $C_1$–$C_{18}$ alkyl, $C_3$–$C_7$ cycloalkyl, alkyl or aralkly group selected from the group consisting of phenyl-$C_1$–$C_4$ alkyl, naphthyl-$C_1$–$C_4$, phenyl and naphthyl, wherein these groups are optionally substituted by the corresponding substituents of $R^8$ and $R^9$, and
$R^{11}$ represents the radical of a coupling component selected from the group consisting of benzene, naphthalene, acetoacetarylide, pyrazole, and pyridone coupling components, or a phenyl group which is optionally substituted by Cl, Br, F, $C_1$-$C_6$-alkyl or $C_1$-$C_6$-alkoxy.

2. Compounds according to claim 1, of the formula

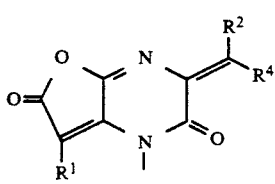

(III)

3. Compounds according to claim 1, of the formula

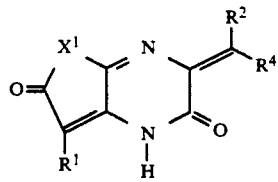

VI

4. Compounds according to claim 1, of the formula

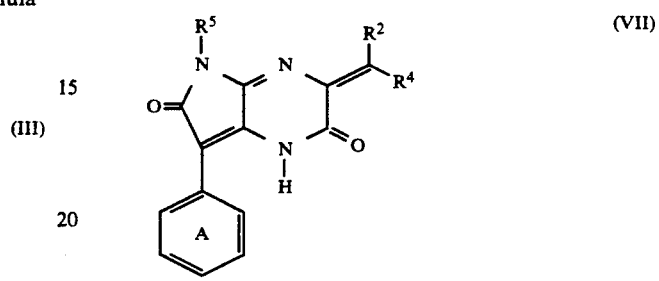

(VII)

in which the ring designated by A is optionally substituted by halogen, —$NHCOR^6$, $NR^8R^9$.

* * * * *

UNITED STATES PATENT AND TRADEMARK OFFICE
CERTIFICATE OF CORRECTION

PATENT NO. : 5,241,068
DATED     : August 31, 1993
INVENTOR(S) : Diblitz, et al.

It is certified that error appears in the above-indentified patent and that said Letters Patent is hereby corrected as shown below:

Col. 1, line 30    Delete " 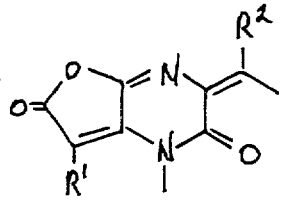 " and substitute 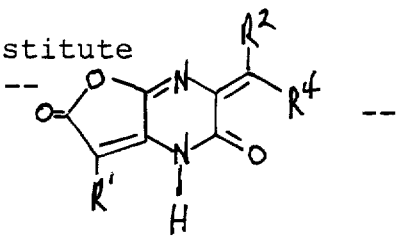 --

Col. 20, line 20, (claim 1, line 10, after Formula II) after "OR$^7$" insert --,--.

Col. 21, line 20   Delete " 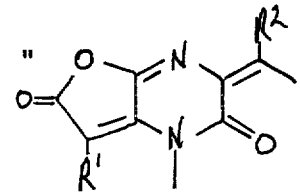 and substitute

UNITED STATES PATENT AND TRADEMARK OFFICE
CERTIFICATE OF CORRECTION

PATENT NO. : 5,241,068
DATED : August 31, 1993
INVENTOR(S) : Diblitz, et al.

It is certified that error appears in the above-indentified patent and that said Letters Patent is hereby corrected as shown below:

Col. 21, line 20
Cont'd           -- 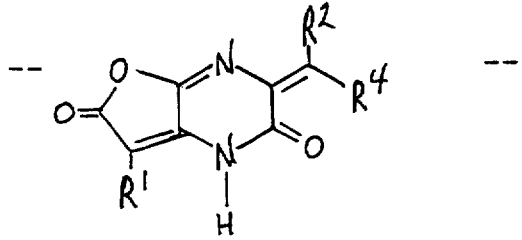 --

Signed and Sealed this

Thirtieth Day of May, 1995

Attest:

BRUCE LEHMAN

Attesting Officer    Commissioner of Patents and Trademarks